US006251139B1

(12) United States Patent
Lin et al.

(10) Patent No.: US 6,251,139 B1
(45) Date of Patent: Jun. 26, 2001

(54) ORTHOPEDIC FILLING MATERIAL AND METHOD OF USE THEREOF

(76) Inventors: Chih-I Lin, 14292 Spring Vista La., Chino Hills, CA (US) 91709; Shengfu Lin, 3F, 7, Lane 110, Chein-Kang Street, Taipei (TW)

( * ) Notice: Subject to any disclaimer, the term of this patent is extended or adjusted under 35 U.S.C. 154(b) by 0 days.

(21) Appl. No.: 09/576,969

(22) Filed: May 24, 2000

(30) Foreign Application Priority Data

Jan. 13, 2000 (TW) ................................. 89100500

(51) Int. Cl.⁷ ............................... A61F 2/44; A61B 19/00
(52) U.S. Cl. .................................. 623/17.11; 623/16.11; 128/898
(58) Field of Search ............................. 623/17.11, 16.11; 433/180; 128/898

(56) References Cited

U.S. PATENT DOCUMENTS

| | | | | |
|---|---|---|---|---|
| 4,619,655 | * | 10/1986 | Hanker et al. ........................... | 623/1 |
| 4,843,112 | * | 6/1989 | Gerhart et al. ......................... | 523/114 |
| 5,385,887 | * | 1/1995 | Yim et al. ............................... | 514/12 |
| 5,425,769 | * | 6/1995 | Snyders, Jr. ............................ | 623/16 |
| 5,947,893 | * | 9/1999 | Agrawal et al. ........................ | 600/36 |
| 6,005,162 | * | 12/1999 | Constantz ............................... | 623/16 |

* cited by examiner

Primary Examiner—Dinh X. Nguyen
Assistant Examiner—Urmi Chattopadhyay
(74) Attorney, Agent, or Firm—Bacon & Thomas

(57) ABSTRACT

A method of using a plaster of Paris as an orthopedic filling material prepared by mixing 15–80% by weight of calcium sulfate half-hydrate and 85–20% by weight of water, an aqueous solution, an aqueous dispersion, or an aqueous suspension; and stirring the resulting mixture into a paste having a viscosity in the range of 20 and 75 poises. The paste is injected into a cavity of a bone or a vertebra to be reinforced. The injected paste becomes hard in the cavity, and eventually will be absorbed by the patient.

8 Claims, No Drawings

ORTHOPEDIC FILLING MATERIAL AND METHOD OF USE THEREOF

FIELD OF THE INVENTION

The present invention relates generally to an orthopedic filling material, and more particularly to an orthopedic filling material prepared from plaster of Paris having a specific viscosity, and the method of use of the orthopedic filling material.

BACKGROUND OF THE INVENTION

The bone cement is one of the important orthopedic filling materials and is used for filling the bone marrow gap in the orthopedic surgery, and the gap between the bone and the implant, thereby enabling the bone to have an appropriate strength after the surgery, or enabling the implant to be joined intimately with the bone. However, the bone cement is incapable of being absorbed by a human body and is apt to affect the blood-making function of the marrow.

The bone graft is another one of the important orthopedic filling materials. The advantage of the bone graft is that it is capable of promoting the bone ingrowth. However, the bone graft must be accompanied with an implant in view of the fact that the bone graft is incapable of bearing the burden of the pressure of the body weight of a patient prior to its fusion with the bone.

The synthetic orthopedic granule is also one of the important orthopedic filling materials; nevertheless, it shares with the bone graft the same drawback described above.

SUMMARY OF THE INVENTION

An objective of the present invention is to provide a calcium sulfate-containing orthopedic filling material having a specific viscosity.

Another objective of the present invention is to provide a method of using a plaster of Paris as an orthopedic filling material for the treatment of a deformed bone in a patient, wherein said plaster of Paris is a paste having a viscosity ranging from 20 to 75 poises, and preferably, ranging from 30 to 60 poises.

DETAILED DESCRIPTION OF THE INVENTION

An orthopedic filling material made of plaster of Paris is disclosed in the present invention, which is a paste having a viscosity ranging from 20 to 75 poises, and preferably, ranging from 30 to 60 poises.

A suitable process for preparing the paste of the present invention comprises mixing 15–80%, preferably 20–75%, and more preferably 30–60%, by weight of calcium sulfate half-hydrate ($CaSO_4 \cdot 0.5H_2O$) and 85–20% by weight of water, an aqueous solution, an aqueous dispersion, or an aqueous suspension; stirring the resulting mixture into a paste. The resulting paste is rested for a period of time to have a desired viscosity.

A treatment of a deformed bone according to the present invention comprises injecting said paste into a cavity of a born or a vertebra, which requires treatment, as an orthopedic filling material, so that the injected paste will become hard in said cavity, and eventually will be absorbed by the patient.

Preferably, said paste of the present invention comprises 15–80%, more preferably 20–75%, and most preferably 30–60% by weight of calcium sulfate; and water, an aqueous solution, an aqueous dispersion, or an aqueous suspension as the balance.

The water used in the present invention can be distilled water, reverse-osmosis water, or pure water produced by other means.

The aqueous solution used in the present invention may contain certain remedial drugs (such as antibiotics, and bone ingrowth drugs), nutrients, or other additives.

The aqueous dispersion used in the present invention may contain remedial drugs (such as antibiotics, and bone ingrowth drugs), nutrients, or other additives, which are dispersed in water with a dispersing agent.

The aqueous suspension used in the present invention may contain remedial drugs (such as antibiotics, and bone ingrowth drugs), nutrients, or other additives.

In the process for preparing the paste of the present invention, drugs or nutrients may be added before the mixing or in the midst of the mixing such that they are mixed with the calcium sulfate half-hydrate and water, the aqueous solution, the aqueous dispersion or the aqueous suspension.

The drugs, nutrients, and additives may be in the form of solid, liquid, or gas. The drugs and nutrients added should not have adverse effect on the hardening of the paste. The additives can have a direct effect or an indirect effect on the paste, such as hardening promoters, hardening delaying agents, and the like.

The paste of the present invention has a viscosity ranging between 20 and 75 poises, preferably between 30 and 60 poises. If the viscosity of the paste is too low, the paste is apt to disperse quickly into the body fluid before the paste solidifies in the cavity of the bone or vertebra. If the viscosity of the paste is excessively high, the paste can not be easily injected into the cavity of the bone or vertebra.

The chemical formula of the calcium sulfate half-hydrate used in preparing the paste of the present invention consists essentially of $CaSO_4 \cdot 0.5H_2O$. The chemical formula of the calcium sulfate of the paste of the present invention is a mixture of $CaSO_4 \cdot nH_2O$, in which n has a value of 0, 0.5, 2, or others.

The viscosity of the paste of the present invention is measured by a RVS-1 Rotary viscometer available from Fargo Company, Taipei, Taiwan.

EXAMPLES 1–12

A paste was formed by mixing at 30 rpm for one minute at 27° C. 10 grams of the half-water calcium sulfate and 3.6 ml of pure water. The paste was rested without disturbance. 5 ml of paste was then taken out with an injector having an injection outlet inner diameter of 0.8 mm at different take-out time, and immediately injected on a bottom of a beaker containing 100 ml saline water. Thereafter, the hardening of the injected paste in the saline water was observed 20 minutes after injection. The results are shown in Table 1.

TABLE 1

| Example | Take-out time (min) | Viscosity (poise) | Hardening State[a] | Take-out/Injection Condition[b] |
|---|---|---|---|---|
| 1 | 2 | 14 | X | + |
| 2 | 3 | 20 | Δ | + |
| 3 | 4 | 28 | ΔΔ | + |
| 4 | 5 | 30 | ◯ | + |
| 5 | 8 | 31 | ◯ | + |
| 6 | 10 | 32 | ◯ | + |
| 7 | 11 | 48 | ◯ | + |
| 8 | 12 | 55 | ◯ | + |
| 9 | 13 | 58 | ◯ | + |

TABLE 1-continued

| Example | Take-out time (min) | Viscosity (poise) | Hardening State[a] | Take-out/Injection Condition[b] |
|---|---|---|---|---|
| 10 | 14 | 67 | ○ | − |
| 11 | 15 | 70 | ○ | − |
| 12 | 16 | 80 | ○ | − − |

[a]
X: no hardening, the injected paste disperses
Δ: the injected paste becomes flat and hard
ΔΔ: the bottom of the injected paste becomes bigger and hard
○: the injected paste become hard with substantially no change in shape
[b]
+: take-out and injection without problem
−: injection being slightly difficult
− −: injection being extremely difficult

EXAMPLES 13–20

These examples were similar to Examples 1–12, except that the agitation time was changed to 30 seconds, and that the temperature was changed to 30° C. The results are shown in Table 2.

TABLE 2

| Example | Take-out time (min) | Viscosity (poise) | Hardening State[a] | Take-out/Injection Condition[b] |
|---|---|---|---|---|
| 13 | 4 | 27 | ΔΔ | + |
| 14 | 5 | 30 | ○ | + |
| 15 | 6 | 31 | ○ | + |
| 16 | 7 | 42 | ○ | + |
| 17 | 8 | 56 | ○ | + |
| 18 | 9 | 72 | ○ | − |
| 19 | 10 | 80 | ○ | − − |
| 20 | 11 | 82 | ○ | − − |

[a], [b] defined as in Table 1

EXAMPLES 21–27

These examples were similar to Examples 1–12, except that the agitation time was 10 seconds, and that the temperature was 30° C., and furthat that 0.9 wt% of sodium chloride solution was used in place of pure water. The results are shown in Table 3.

TABLE 3

| Example | Take-out time (min) | Viscosity (poise) | Hardening State[a] | Take-out/Injection Condition[b] |
|---|---|---|---|---|
| 21 | 10 | 20 | Δ | + |
| 22 | 20 | 30 | ○ | + |
| 23 | 50 | 52 | ○ | + |
| 24 | 80 | 44 | ○ | + |
| 25 | 100 | 56 | ○ | + |
| 26 | 120 | 78 | ○ | − − |
| 27 | 140 | 180 | — | Could not be taken out |

[a], [b] defined as in Table 1

EXAMPLES 28–32

9.5 grams of calcium sulfate half-hydrate and 0.5 gram of hydroxyapatite (HA) were mixed with 3.6 ml of pure water at 29° C. and were agitated for 20 seconds. The paste was rested without disturbance. 5 ml of paste was then taken out with an injector having an injection outlet inner diameter of 0.8 mm at different take-out time, and immediately injected on a bottom of a beaker containing 100 ml saline water. Thereafter, the hardening of the injected paste in the saline water was observed. The results are shown in Table 4.

TABLE 4

| Example | Take-out time (min) | Viscosity (poise) | Hardening State[a] | Take-out/Injection Condition[b] |
|---|---|---|---|---|
| 28 | 30 | 40 | ○ | + |
| 29 | 50 | 52 | ○ | + |
| 30 | 100 | 60 | ○ | + |
| 31 | 120 | 75 | ○ | − |
| 32 | 150 | 90 | ○ | − − |

[a], [b] defined as in Table 1

EXAMPLES 33–40

These examples were similar to Examples 28–32, except that the amount of pure water was increased to 4.8 ml. The results are shown in Table 5.

TABLE 5

| Example | Take-out time (min) | Viscosity (poise) | Hardening State[a] | Take-out/Injection Condition[b] |
|---|---|---|---|---|
| 33 | 200 | 17 | X | + |
| 34 | 210 | 19 | Δ | + |
| 35 | 220 | 25 | ΔΔ | + |
| 36 | 230 | 28 | ΔΔ | + |
| 37 | 240 | 33 | ○ | + |
| 38 | 300 | 42 | ○ | + |
| 39 | 330 | 58 | ○ | + |
| 40 | 340 | 77 | ○ | − − |

[a], [b] defined as in Table 1

EXAMPLES 41–18

These examples were similar to Examples 28–32, except that the amount of pure water was increased to 6 ml. The results are shown in Table 6.

TABLE 6

| Example | Take-out time (min) | Viscosity (poise) | Hardening State[a] | Take-out/Injection Condition[b] |
|---|---|---|---|---|
| 41 | 300 | 20 | X | + |
| 42 | 320 | 21 | Δ | + |
| 43 | 350 | 28 | ΔΔ | + |
| 44 | 400 | 29 | ΔΔ | + |
| 45 | 420 | 32 | ○ | + |
| 46 | 450 | 53 | ○ | + |
| 47 | 480 | 64 | ○ | − |
| 48 | 550 | 85 | ○ | − − |

[a], [b] defined as in Table 1

EXAMPLES 49–50

These examples were similar to Examples 1–12, except that an aqueous suspension containing 0.5% by weight of calcium sulfate dihydrate was used in place of the pure water. The results are shown in Table 7.

TABLE 7

| Example | Take-out time (min) | Viscosity (poise) | Hardening State[a] | Take-out/Injection Condition[b] |
|---|---|---|---|---|
| 49 | 30 | 35 | ○ | + |
| 50 | 60 | 48 | ○ | + |

[a], [b] defined as in Table 1

What is claimed is:

1. A method of treating a deformed bone in a patient, comprising injecting a plaster of Paris into a cavity of a bone or a vertebra of said patient, which require treatment, as an orthopedic filling material, so that the injected paste will become hard in said cavity, and eventually will be absorbed by the patient, wherein said plaster of Paris is a paste having a viscosity ranging from 20 to 75 poises.

2. The method as defined in claim 1, wherein said paste has a viscosity ranging between 30 and 60 poises.

3. The method as defined in claim 1, wherein said paste comprises 15–80% by weight of calcium sulfate; and water, an aqueous solution, an aqueous dispersion, or an aqueous suspension as the balance.

4. The method as defined in claim 3, wherein said paste comprises 20–75% by weight of calcium sulfate.

5. The method as defined in claim 4, wherein said paste comprises 30–60% by weight of calcium sulfate.

6. The method as defined in claim 1, wherein said paste is prepared by mixing 15–80% by weight of calcium sulfate half-hydrate ($CaSO_4 \cdot 0.5H_2O$) and 85–20% by weight of water, an aqueous solution, an aqueous dispersion, or an aqueous suspension; and stirring the resulting mixture into a paste.

7. The method as defined in claim 6, wherein 20–75% by weight of calcium sulfate half-hydrate is mixed.

8. The method as defined in claim 7, wherein 30–60% by weight of calcium sulfate half-hydrate is mixed.

* * * * *